US012697250B2

(12) United States Patent (10) Patent No.: US 12,697,250 B2
Govari (45) Date of Patent: Aug. 4, 2026

(54) METHOD AND SYSTEM FOR CATARACT REMOVAL

(71) Applicant: JOHNSON & JOHNSON SURGICAL VISION, INC., Irvine, CA (US)

(72) Inventor: Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 666 days.

(21) Appl. No.: 17/971,936

(22) Filed: Oct. 24, 2022

(65) Prior Publication Data

US 2024/0130891 A1 Apr. 25, 2024
US 2024/0225895 A9 Jul. 11, 2024

(51) Int. Cl.
*A61F 9/007* (2006.01)
*G06N 20/00* (2019.01)
*A61B 17/00* (2006.01)

(52) U.S. Cl.
CPC ......... *A61F 9/00745* (2013.01); *G06N 20/00* (2019.01); *A61B 2017/00057* (2013.01)

(58) Field of Classification Search
CPC ................. A61F 9/00745; A61F 9/007; A61B 17/320068–2017/320098
See application file for complete search history.

(56) References Cited

U.S. PATENT DOCUMENTS 527,947 A 10/1894 Mcdonell et al.
4,826,482 A 5/1989 Kamen 4,954,960 A 9/1990 Lo et al.
5,157,603 A 10/1992 Scheller et al.
5,160,317 A 11/1992 Costin
(Continued)

FOREIGN PATENT DOCUMENTS

DE 3234621 A1 3/1984
EP 0741554 A1 11/1996
(Continued)

OTHER PUBLICATIONS

U.S. Appl. No. 16/727,100, titled "Phacoemulsification Apparatus," filed Dec. 26, 2019.

(Continued)

*Primary Examiner* — Brigid K Byrd

(57) ABSTRACT

A phacoemulsification system, method and computer program product, the system comprising: a phacoemulsification probe having at its distal end a needle to be inserted into an eye, the probe comprising an ultrasonic transducer; an optical fiber transferring light from a source and having a distal end positioned in proximity to the tip of the needle for emitting light of predetermined frequency or pattern; a light sensor for detecting the light; and a processor, for repeatedly: receive from the sensor an indication of the detected light; determine whether the detected light complies with a condition indicating contact between the needle and a lens of the eye; subject to determining compliance with the condition and that the ultrasonic transducer being inactive, toggle the ultrasonic transducer ON; and subject to determining that the detected light does not comply with the condition and that the ultrasonic transducer being active, toggle the ultrasonic transducer OFF.

17 Claims, 5 Drawing Sheets

(56) References Cited

U.S. PATENT DOCUMENTS

| | | | |
|---|---|---|---|
| 5,279,547 A * | 1/1994 | Costin | A61F 9/00745 |
| | | | 604/22 |
| 5,733,256 A | 3/1998 | Costin | |
| 5,836,990 A | 11/1998 | Li | |
| 6,690,280 B2 | 2/2004 | Citrenbaum et al. | |
| 7,727,193 B2 | 6/2010 | Boukhny et al. | |
| 7,842,005 B2 | 11/2010 | Kadziauskas et al. | |
| 8,048,020 B2 | 11/2011 | Boukhny et al. | |
| 8,246,580 B2 | 8/2012 | Hopkins et al. | |
| 8,414,605 B2 | 4/2013 | Gordon et al. | |
| 8,523,812 B2 | 9/2013 | Boukhny et al. | |
| 8,597,228 B2 | 12/2013 | Pyles et al. | |
| 9,144,517 B2 | 9/2015 | Kuebler et al. | |
| 9,282,989 B2 | 3/2016 | Boukhny et al. | |
| 9,522,221 B2 | 12/2016 | Muri et al. | |
| 9,545,335 B2 | 1/2017 | Boukhny et al. | |
| 9,707,127 B2 | 7/2017 | Kadziauskas | |
| 9,999,710 B2 | 6/2018 | Ross et al. | |
| 10,045,882 B2 | 8/2018 | Balicki et al. | |
| 10,070,988 B2 | 9/2018 | McDonell et al. | |
| 10,219,940 B2 | 3/2019 | Raney et al. | |
| 10,368,760 B2 | 8/2019 | Hauck | |
| 10,453,571 B2 | 10/2019 | Teodorescu | |
| 10,463,780 B2 | 11/2019 | Mallough et al. | |
| 10,596,033 B2 | 3/2020 | Urich et al. | |
| 10,940,039 B2 | 3/2021 | Banko | |
| 11,141,313 B2 | 10/2021 | Zhang et al. | |
| 11,317,937 B2 | 5/2022 | Nott et al. | |
| 11,399,858 B2 | 8/2022 | Sawhney et al. | |
| 11,464,559 B2 | 10/2022 | Nott et al. | |
| 11,589,888 B2 | 2/2023 | Shelton, IV et al. | |
| 11,612,408 B2 | 3/2023 | Yates et al. | |
| 12,127,979 B2 | 10/2024 | Gliner et al. | |
| 2004/0092800 A1 | 5/2004 | Mackool | |
| 2004/0193182 A1 | 9/2004 | Yaguchi et al. | |
| 2005/0209560 A1 * | 9/2005 | Boukhny | A61M 3/0258 |
| | | | 604/122 |
| 2005/0261628 A1 | 11/2005 | Boukhny et al. | |
| 2006/0079788 A1 | 4/2006 | Anderson et al. | |
| 2006/0100570 A1 | 5/2006 | Urich et al. | |
| 2006/0129140 A1 | 6/2006 | Todd et al. | |
| 2006/0224107 A1 | 10/2006 | Claus et al. | |
| 2007/0073309 A1 | 3/2007 | Kadziauskas et al. | |
| 2007/0161972 A1 | 7/2007 | Felberg et al. | |
| 2008/0014702 A1 | 1/2008 | Kumar et al. | |
| 2008/0064935 A1 | 3/2008 | Wong et al. | |
| 2008/0147023 A1 | 6/2008 | Hopkins et al. | |
| 2009/0118663 A1 | 5/2009 | Rockley et al. | |
| 2009/0182266 A1 | 7/2009 | Gordon et al. | |
| 2010/0069825 A1 | 3/2010 | Raney | |
| 2010/0118266 A1 | 5/2010 | Nixon | |
| 2010/0287127 A1 | 11/2010 | Claus et al. | |
| 2011/0015563 A1 | 1/2011 | Boukhny | |
| 2011/0092896 A1 | 4/2011 | Kuebler et al. | |
| 2011/0112472 A1 | 5/2011 | Jacobson et al. | |
| 2011/0144641 A1 | 6/2011 | Dimalanta, Jr. et al. | |
| 2011/0313280 A1 | 12/2011 | Govari et al. | |
| 2012/0197215 A1 | 8/2012 | Akahoshi | |
| 2012/0232466 A1 | 9/2012 | Kuebler et al. | |
| 2013/0211435 A1 | 8/2013 | Boukhny et al. | |
| 2014/0018724 A1 | 1/2014 | Staggs | |
| 2014/0114296 A1 | 4/2014 | Woodley et al. | |
| 2014/0257172 A1 | 9/2014 | Yalamanchili | |
| 2014/0316254 A1 | 10/2014 | Eversull et al. | |
| 2014/0323953 A1 | 10/2014 | Sorensen et al. | |
| 2015/0045806 A1 | 2/2015 | Urich et al. | |
| 2015/0073816 A1 | 3/2015 | Ha et al. | |
| 2015/0148615 A1 | 5/2015 | Brennan et al. | |
| 2015/0216726 A1 | 8/2015 | Kadziauskas et al. | |
| 2016/0175149 A1 * | 6/2016 | McDonell | A61F 9/00745 |
| | | | 600/249 |
| 2016/0175543 A1 | 6/2016 | Frankhouser et al. | |
| 2017/0312431 A1 * | 11/2017 | Johnson | A61F 9/007 |
| 2018/0028359 A1 | 2/2018 | Gordon et al. | |
| 2018/0092555 A1 | 4/2018 | Script | |
| 2018/0168768 A1 * | 6/2018 | Mirsepassi | A61F 9/008 |
| 2018/0207330 A1 | 7/2018 | Ovchinnikov et al. | |
| 2018/0318131 A1 | 11/2018 | Boukhny et al. | |
| 2019/0099526 A1 | 4/2019 | Hajishah et al. | |
| 2019/0133822 A1 | 5/2019 | Banko | |
| 2019/0274748 A1 | 9/2019 | Danziger et al. | |
| 2020/0107957 A1 | 4/2020 | Zhang | |
| 2020/0107958 A1 | 4/2020 | Wong et al. | |
| 2020/0309760 A1 | 10/2020 | Durant | |
| 2021/0045918 A1 | 2/2021 | Raney | |
| 2021/0196515 A1 | 7/2021 | Urich | |
| 2021/0330493 A1 | 10/2021 | Steen et al. | |
| 2021/0361481 A1 | 11/2021 | Gliner et al. | |
| 2021/0401623 A1 | 12/2021 | Zhang et al. | |
| 2022/0008251 A1 | 1/2022 | Govari et al. | |
| 2022/0133534 A1 * | 5/2022 | Duval | G08C 17/00 |
| | | | 606/170 |
| 2022/0192876 A1 | 6/2022 | Algawi et al. | |
| 2022/0192878 A1 | 6/2022 | Algawi et al. | |
| 2022/0313489 A1 | 10/2022 | Hajishah et al. | |
| 2022/0362452 A1 | 11/2022 | Algawi et al. | |
| 2023/0039808 A1 | 2/2023 | Govari et al. | |
| 2023/0043082 A1 | 2/2023 | Govari et al. | |
| 2023/0210692 A1 | 7/2023 | Casutt et al. | |
| 2023/0218438 A1 * | 7/2023 | Nahum | A61F 9/00745 |
| | | | 606/107 |
| 2023/0285189 A1 | 9/2023 | Govari | |
| 2023/0320897 A1 | 10/2023 | Hajishah et al. | |
| 2024/0099884 A1 | 3/2024 | Govari et al. | |
| 2024/0148955 A1 * | 5/2024 | Perkins | A61F 9/00736 |
| 2024/0197173 A1 | 6/2024 | Kok et al. | |
| 2024/0398618 A1 | 12/2024 | Gliner et al. | |
| 2025/0009556 A1 | 1/2025 | Waid et al. | |

FOREIGN PATENT DOCUMENTS

| | | |
|---|---|---|
| EP | 0956840 A2 | 11/1999 |
| EP | 1935383 A1 | 6/2008 |
| EP | 1765190 B1 | 7/2008 |
| EP | 1743309 B1 | 10/2011 |
| EP | 3448235 A2 | 3/2019 |
| EP | 3260065 B1 | 2/2020 |
| JP | 4126304 B2 | 7/2008 |
| WO | 9211814 A1 | 7/1992 |
| WO | 2008016870 A2 | 2/2008 |
| WO | 2010014937 A1 | 2/2010 |
| WO | 2016122790 A1 | 8/2016 |
| WO | 2017187380 A2 | 11/2017 |
| WO | 2019069201 A1 | 4/2019 |
| WO | 2021119616 A1 | 6/2021 |
| WO | 2023170486 A1 | 9/2023 |

OTHER PUBLICATIONS

U.S. Appl. No. 17/357,587, titled, "Accurate Irrigation Rate Measurement System and Method," filed Jun. 24, 2021.

* cited by examiner

METHOD AND SYSTEM FOR CATARACT REMOVAL

FIELD OF THE DISCLOSURE

This disclosure relates generally to cataract removal, and specifically to a method for operating an ultrasonic transducer during a phacoemulsification operation.

BACKGROUND OF THE DISCLOSURE

A cataract is a clouding and hardening of the eye's natural lens, which often happens when people get older. A common treatment of cataract is phacoemulsification cataract surgery. In the procedure, a portion of the anterior surface of the lens capsule is removed to gain access to the cataract. The surgeon then uses a phacoemulsification probe, which is an ultrasonic handpiece with a needle. The tip of the needle vibrates at ultrasonic frequency, which emulsifies the cataract lens. At a same time, a pump aspirates particles and fluid from the eye through the tip, wherein the aspirated fluids are replaced with irrigation of a balanced salt solution to maintain the intraocular pressure in the anterior chamber of the eye. After removing the cataract with phacoemulsification, the softer outer lens cortex is removed with suction. An intraocular lens (IOL) is then introduced into the empty lens capsule restoring the patient's vision.

BRIEF DESCRIPTION OF THE DRAWINGS

The present disclosure will be more fully understood from the following detailed description of the examples thereof, taken together with the drawings, in which.

DETAILED DESCRIPTION OF EXAMPLES

Figure 1A:
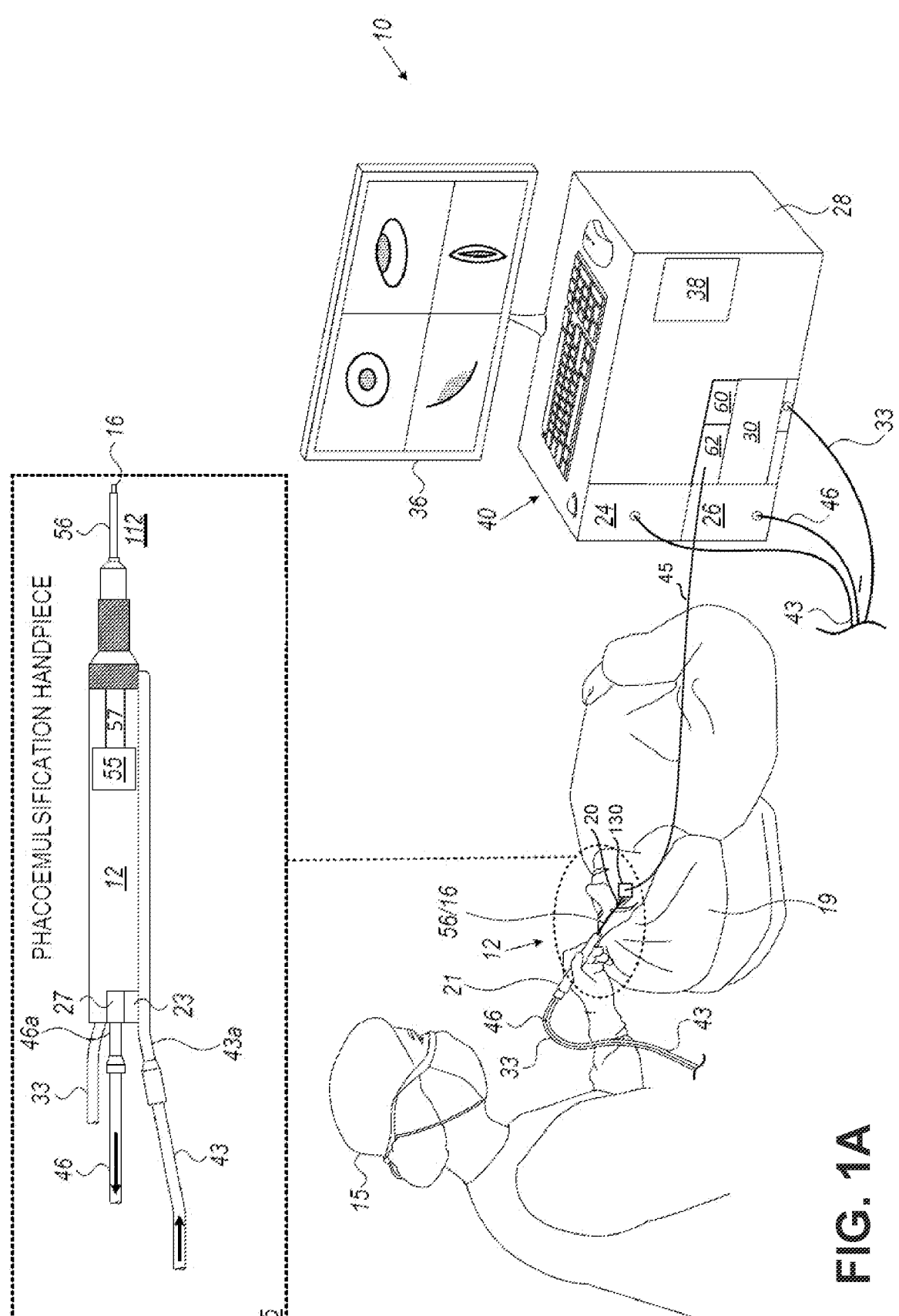
FIG. 1A is a schematic, pictorial view, along with an orthographic side view, of a phacoemulsification apparatus, in accordance with an example of the present disclosure.

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

In the description below, the term "about" as related to numerical values may include values that are in the range of +/−10% of the indicated value.

Overview

Cataract is often handled by a Phacoemulsification procedure, in which an ultrasonic handpiece is used to insert a needle into the patient's eye, wherein the tip of the needle can vibrate at ultrasonic frequency, to emulsify the cataract.

However, operating the ultrasound transducer over the entire procedure is energy consuming, wasteful, and may have negative repercussions on the patient, without any advantage.

Optionally, the ultrasound transducer is manually activated and deactivated by the operating physician, using for example a foot pedal, a switch, or the like. The physician may activate and deactivate the ultrasound transducer based on visual inspection of the needle location relative to the lens, i.e., the physician activates the ultrasound transducer when the needle is in contact with the lens and deactivates it when the needle is not in contact with the lens.

Since the eye area is rather small, identifying the exact timing at which the needle contacts the lens may be difficult and may lead to activating the ultrasound transducer before or after contact is made, or deactivating the ultrasound transducer before or after contact is lost. Each of these cases may result in suboptimal results, for example the operation may be less efficient and may take longer.

Therefore, it may be beneficial to automate toggling of the ultrasonic transducer on and off when the needle makes or loses, respectively, contact with the lens being emulsified, such that the operation will be performed in a more efficient manner and without repercussions on the patient.

In order to limit the operation of the ultrasonic transducer to the contact times, it is required to detect when the needle is in contact with the lens. The ultrasonic transducer can then be operated only on the required periods of time, when it can promote the effect of emulsifying the lens.

During the procedure, contact between the needle and the lens is typically intermittent, i.e., the needle is alternately in and out of contact with the lens. Therefore, identifying the engagement and the disengagement of the needle from the lens needs to be performed with a fast response time, i.e., with minimal latency, such that the ultrasonic transducer will be active substantially in synchronization with the needle being in contact with the lens. This is particularly helpful in utilizing even short periods of time during which the needle is in contact with the lens to effect emulsification, and avoiding ineffective activation when there is no contact.

In some exemplary embodiments, the contact between the needle and the lens may be assessed using an optical signal, also referred to as "light".

A light source may be positioned in or near the phacoemulsification probe, directed near the tip of the needle, and may emit an optical signal in one or more directions, for example in a direction coinciding with or substantially parallel and in close proximity to the needle. The light may be of a predefined wavelength or wavelength range, and emitted at a defined pattern, for example a pattern of pulses of defined duration at defined frequency.

A light sensor that is sensitive to the wavelength of the light source, may be positioned externally to the eye of the patient, for example in proximity to the eye, such that it may receive light from inside the eye, emitted by the light source. The light sensor may be implemented as a photodiode or a one-dimensional or two-dimensional array of photo diodes for capturing an optic signal in response to the light emitted by the light source.

When the needle is in close proximity to, or in contact with the lens, the optical signal may be fully or partially obstructed, absorbed by the lens or other organs of the eye, blocked, or reflected back into the needle by the lens. Thus, in this situation the light sensor will receive no or low amplitude light in the wavelength and pattern of the emitted light. As the needle is farther from the lens, a stronger optical signal will be scattered or reflected from different areas of the lens or other parts of the eye, and received by the light sensor.

Thus, the contact of the needle with the lens may be determined by the amount and/or spatial distribution of the light received by the sensor, in response to the light emitted by the light source.

A Controller may toggle the light source in a predefined temporal manner. The amount of light sensed by the light sensor in the relevant wavelength may be processed by the controller while considering the timing of the controller toggling the light source ON and OFF. For example, the controller may use the light measurement at times where the light source is OFF to assess the light attributed to the environment. In some examples, the light source may be toggled at a frequency of 50-200 Hz, e.g., 100 Hz. The controller may be a dedicated microcontroller rather than a central processing unit (CPU) of the apparatus, so as to enable fast response time without engaging the CPU's hardware or software.

The controller may thus toggle the light source ON and OFF, and may determine based on the amount or spatial pattern of light sensor as measured during the times the light source was ON, whether the needle is in contact with the lens or not. The controller, or another controller, may also be adapted to toggle ON/OFF the ultrasound transducer as required.

Whether the reflected light indicates that the needle is contacting the lens or not, may be determined in a multiplicity of ways. In some embodiments, such determination may be based upon the existence of one or more conditions.

In one example, a luminance threshold may be determined, whether to the whole sensor or to pixel groups comprising one or more pixels. If the total luminance output by the sensor in the relevant wavelength at the illumination periods is below the threshold, it is assumed that the needle is in contact with the lens, and the ultrasonic transducer should be active. The ultrasound transducer may keep operating as long as the luminance is below the threshold. When the luminance increases above the threshold, it is assumed that the needle disengaged from the lens, and the ultrasound transducer may be deactivated. The ultrasound transducer may then be operated again once the needle resumes contact with the lens and the luminance decreases again to a value below the threshold.

In another example, since the initial state of the needle is that it is not in contact with the lens, then a baseline of the luminance upon the needle entering the eye is expected to be at some level. When the luminance drops below the baseline in at least a predetermined ratio, for example about 50%-100%, e.g., 80%, it may be determined that the needle has made contact with the lens, and vice versa.

In further embodiments, the rate of change in the luminance may also be considered, such that a sharp change, e.g., subject to the luminance derivative dropping below a first predetermined value or increasing above a second predetermined value, it may be determined that the needle engaged with or disengaged from the lens, respectively.

In some embodiments, determining whether the needle is in contact with the lens may be based on an artificial intelligence (AI) engine, such as a Neural Network, a Deep Neural Network, or other engines. The engine may be trained using supervised learning upon a plurality of measurements performed over one or more operations. For example, the luminance and possibly its distribution over the pixels of the light sensor may be measured during each training operation. The label (i.e., the ground truth) associated with each measurement is whether the needle contacts the lens or not, as can be deduced from the physician activating the ultrasound transducer or not, or by any other system or method. The engine is thus trained, such that upon a given luminance value or spatial distribution over the sensor pixels (and possibly additional data such as previous values), the engine outputs whether the needle is in contact with the lens or not.

In some embodiments, each operation may start with a short training session in which the engine is trained upon the reflected light and the physician starting and stopping the ultrasound transducer when the needle is or is not in contact with the lens. The AI engine may thus be trained for the particular settings, including for example where the light sensor is positioned relative to the eye, the specific properties of the patient's eye, or the like. The operation may then continue with automatic activation and deactivation of the ultrasound transducer in response to the amount and/or distribution of light in the relevant wavelength received by the sensor, as determined by the AI engine.

It is appreciated that in any of the above embodiments, not only the total amount of light measured by the sensor, but also its spatial distribution over the light sensor may also be considered as a factor in determining whether the needle is in contact with the lens or not.

In some embodiments, a drive module may operate and control the ultrasound transducer, wherein the controller can enable or disable the operation of the ultrasound transducer. In some embodiments, the controller and the drive module may be implemented as a single controller, while in other embodiments they may be implemented as separate controllers.

The current disclosure thus provides for activating the ultrasound transducer when its operation is effective in emulsifying the cataract, thereby saving energy, as well as avoiding negative repercussions on the patient.

Additionally, the rate of change of the received light when the needle makes or loses contact with the lens is high relative to the rate of motion of the physician holding the device. Therefore, the fast response time enabled by determining the luminance and hence whether the needle is in contact with the lens, provides for efficient usage of the system, including utilizing even short periods of time in which the needle is in contact with the lens.

System Description

Referring now to FIG. 1A, showing an exemplary phacoemulsification apparatus 10, which includes a phacoemulsification probe 12 having at its distal end 112 a needle 16 which may comprise an optical fiber therein. Needle 16 is configured to be inserted by a physician 15 into the lens capsule of an eye of a patient 19 to remove a cataract lens. While needle 16 is shown in inset 25 as a straight object, it is appreciated that any suitable needle may be used with phacoemulsification probe 12, for example, a curved or bent tip needle commercially available from Johnson & Johnson Surgical Vision, Inc., Irvine, CA, USA.

System 10 may comprise console 28, comprising a user interface 40, including physical and virtual controls such as a keyboard, a mouse, a touchscreen, a joystick, a foot pedal, a speaker, a microphone, or others, for inputting data or commands to the apparatus, and a processor 38.

Probe 12 may comprise ultrasound transducer 55, e.g., a piezoelectric ultrasound transducer, which is configured to vibrate horn 57 and needle 16 in one or more resonant vibration modes of the combined horn and needle element. During the phacoemulsification procedure, upon the application of one or more drive signals to ultrasound transducer 55, the vibration of needle 16 is used to emulsify the cataract. Ultrasound transducer 55 and horn 57, or different combinations providing the same effect are collectively referred to as an ultrasound transducer.

In some embodiments, probe 12 may further comprise a coaxial irrigation sleeve 56 that at least partially surrounds needle 16. During the phacoemulsification procedure, an irrigation pump 24 which may be controlled by processor 38 detailed below may pump irrigation fluid from an irrigation reservoir (not shown) to irrigation sleeve 56, to irrigate the eye. The fluid may be pumped via an irrigation tubing line 43 running from console 28 to an irrigation channel 43a of probe 12.

In some embodiments, eye fluid and waste matter (e.g., emulsified parts of the cataract) are aspirated via a hollow in needle 16 to a collection receptacle (not shown) by an aspiration pump 26, also controlled by processor 38, using aspiration tubing line 46 running from aspiration channel 46a of probe 12 to console 28.

Irrigation pump 24 may be controlled by processor 38 in accordance with readings received from irrigation sensor 23, and aspiration pump 26 may be controlled by processor 38 in accordance with readings received from aspiration sensor 27, to maintain intraocular pressure (IOP) within predetermined limits.

Processor 38 is thus adapted to control the operation of various functions of probe 12 such as the irrigation and aspiration, in accordance with the physician's commands as provided via user interface 40, and with various measurements.

It is appreciated that some or all of the functions of processor 38 may be combined in a single physical component. Alternatively, processor 38 may be implemented using multiple physical components. These physical components may comprise hard-wired or programmable devices, or a combination thereof. In some examples, at least some of the functions of processor 38 may be carried out by suitable software stored in a memory device of processor 38 or console 28. This software may be downloaded to a device in electronic form, over a network, or the like. Alternatively, or additionally, the software may be stored in tangible, nontransitory computer-readable storage media, such as optical, magnetic, or electronic memory.

In an example, the apparatus may comprise a display 36 for displaying various images and aspects of the operation to the physician. In some embodiments, one or more controls of user interface 40 and display 36 may be integrated into a touch screen graphical user interface.

The system may comprise drive module 30 for activating ultrasound transducer 55, for example setting the operation parameters and supplying current to ultrasound transducer 55. Drive module 30 may be realized in hardware or software, for example, in a proportional-integral-derivative (PID) control architecture.

Probe 12 may comprise a light source 104 positioned within or in close proximity to the distal end of needle 16.

In some embodiments, controlled by a controller as detailed below.

In other embodiments, an optical fiber 90 may transfer light from a light source 104 and run through the aspiration hollow in needle 16 such that its distal end emits light in the vicinity of the distal end of needle 16. Light source 104 may be controlled by a controller as detailed below.

The system may comprise light sensor 130 positioned within the operation room such that the light reflected from within the eye hits sensor 130. Light sensor 130 may preferably be located in proximity to the patient's eye, such that it can sense higher amount of the light reflected in response to the light emitted by light source 104.

In some embodiments, sensor 130 may be shaped as an open box or a hemisphere having an opening on a side facing the patient's eye and comprising light sensitive cells on an internal surface. Sensor 130 may be attached to the patient's forehead or nose, or under the patient's eye. In further embodiments, sensor 130 may be held over the eye by a stand.

Light source 104 may emit light in one or more wavelengths or wavelength ranges, such as visible light, InfraRed (IR) light, Near InfraRed light, Ultraviolet light, or any combination thereof. In some embodiments, emitting light in the IR range and using a corresponding light sensor is advantageous in that it ensures that the light measurement is less affected by the ambient light in the operating room.

Light source 104 may emit light constantly, or in a predetermined temporal pattern, such as 50-200 equidistant pulses of 8-80 mSec each per second. The light may travel through optical fiber 90.

The system may comprise controller 60 configured to capture light emitted by light sensor 130, and determine whether the needle is in contact with the lens or not, e.g., based on the amplitude of the signal captured by sensor 130. Controller 60 may also be responsible to control light source 104 to emit light in accordance with the temporal pattern.

Controller 60 may identify whether the timing of the light received by light sensor 130 is in correspondence with the pulses of the light emitted by light source 104, such that the reflected light can be attributed to the emitted light and not to an ambient light. Thus, when the needle is known to be in a distance from the lens, it is expected to observe light in the relevant wavelengths during the pulses, and no such light (or a substantially lesser amount thereof, which may be attributed to ambient light) between the pulses.

Controller 60 may then determine whether the intensity or pattern of light observed during the light pulses indicates that the needle is in contact with the lens or not, according to the criteria mentioned above or as determined by the AI engine.

During phacoemulsification, emulsified lens particles may be aspirated through an aspiration tip, e.g., a hollow within needle 16, then via an aspiration channel of the probe and further proximally into an aspiration line. In some situations, a particle may get caught in the hollow and clog it. Some methods are known for identifying and solving this situation. Since optical fiber 90 runs through the hollow, such particle may also block the light, and cause an erroneous identification of contact between the needle and the lens.

In order to avoid the ultrasound transducer 55 from being active at such situations, controller 60 may be adapted to receive notifications from aspiration sensor 27 indicating a clogging, and disable the activity of ultrasound transducer 55 as long as the hollow is clogged and optionally a period of time afterwards in order to avoid aggressive aspiration of newly released particles.

Additionally, in some embodiments physician 15 may use any control of user interface 40 to set a vibration mode and/or frequency of ultrasound transducer 55, or to override the automatic activation and deactivation by manually starting or stopping the ultrasonic transducer.

The apparatus shown in FIG. 1 may include further elements, which are omitted for clarity of presentation. For example, physician 15 typically performs the procedure using a stereo microscope or magnifying glasses, neither of which are shown. Physician 15 may use other surgical tools in addition to probe 12, which are also not shown in order to maintain clarity and simplicity of presentation.

Figure 1B:
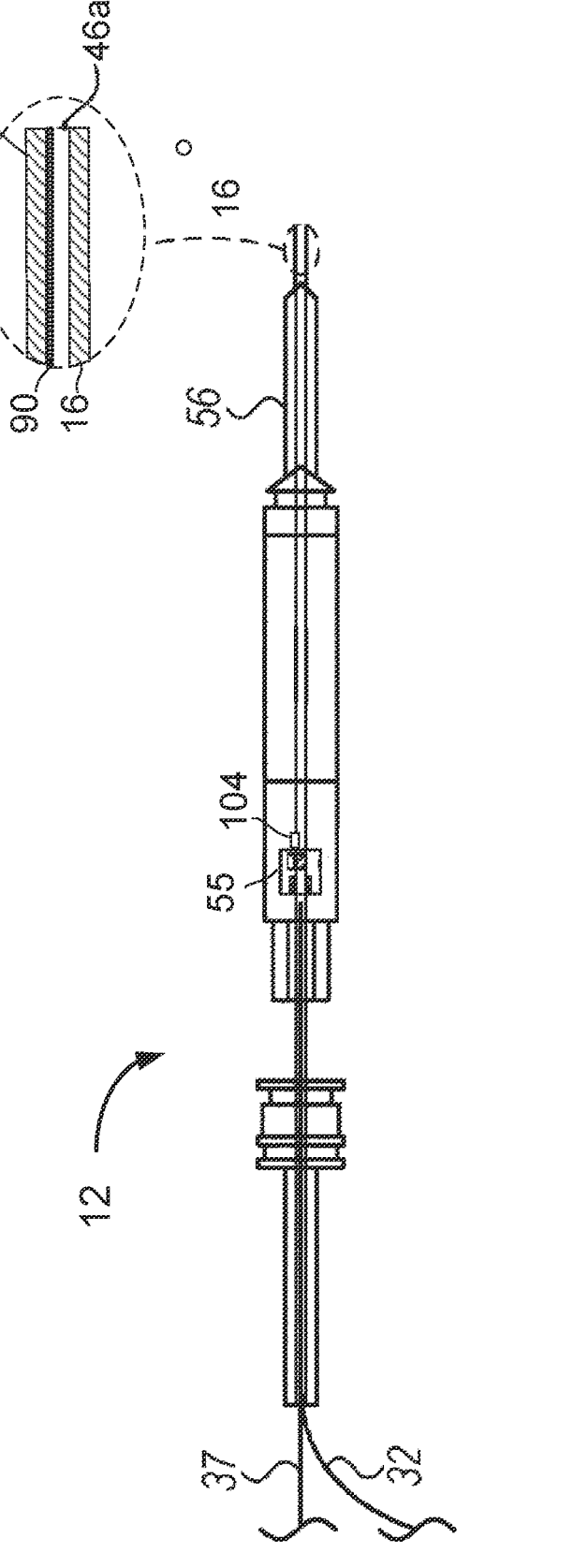
FIG. 1B is a schematic cross section of a probe activated according to light reflection and detection, in accordance with some exemplary embodiments of the disclosure.

Referring now to FIG. 1B, showing a schematic cross section of probe 12, activated according to light reflection and detection, in accordance with some exemplary embodiments of the disclosure.

In some embodiments, probe 12 comprises needle 16 and coaxial irrigation sleeve 56 surrounding needle 16. Needle 16 is hollow and may contain therein an aspiration channel 46a. Aspiration channel 46a may connect with aspiration tube 32 for aspirating the fluids.

In some embodiments, tool 55 comprises one or more ultrasound actuator 55 configured to vibrate responsively to respective driving signals, so as to vibrate needle 16 for breaking the cataract of the patient's eye into small pieces.

In accordance with some embodiments of the disclosure, optic fiber 90 may run through aspiration channel 46a within needle 16. FIG. 1B shows optic fiber 90 attached to a wall of aspiration channel 46a, which may allow for the largest possible continuous volume for aspiration channel 46a. However, this is not mandatory, and optic fiber 90 may also be located adjacent to the wall of aspiration channel 46a. In this implementation the tip of fiber optic 90 located at the distal end of needle 16 serves is the light source.

Light sensor 130 is configured to detect the light received in response to the light emitted by the light source.

Figure 2A:
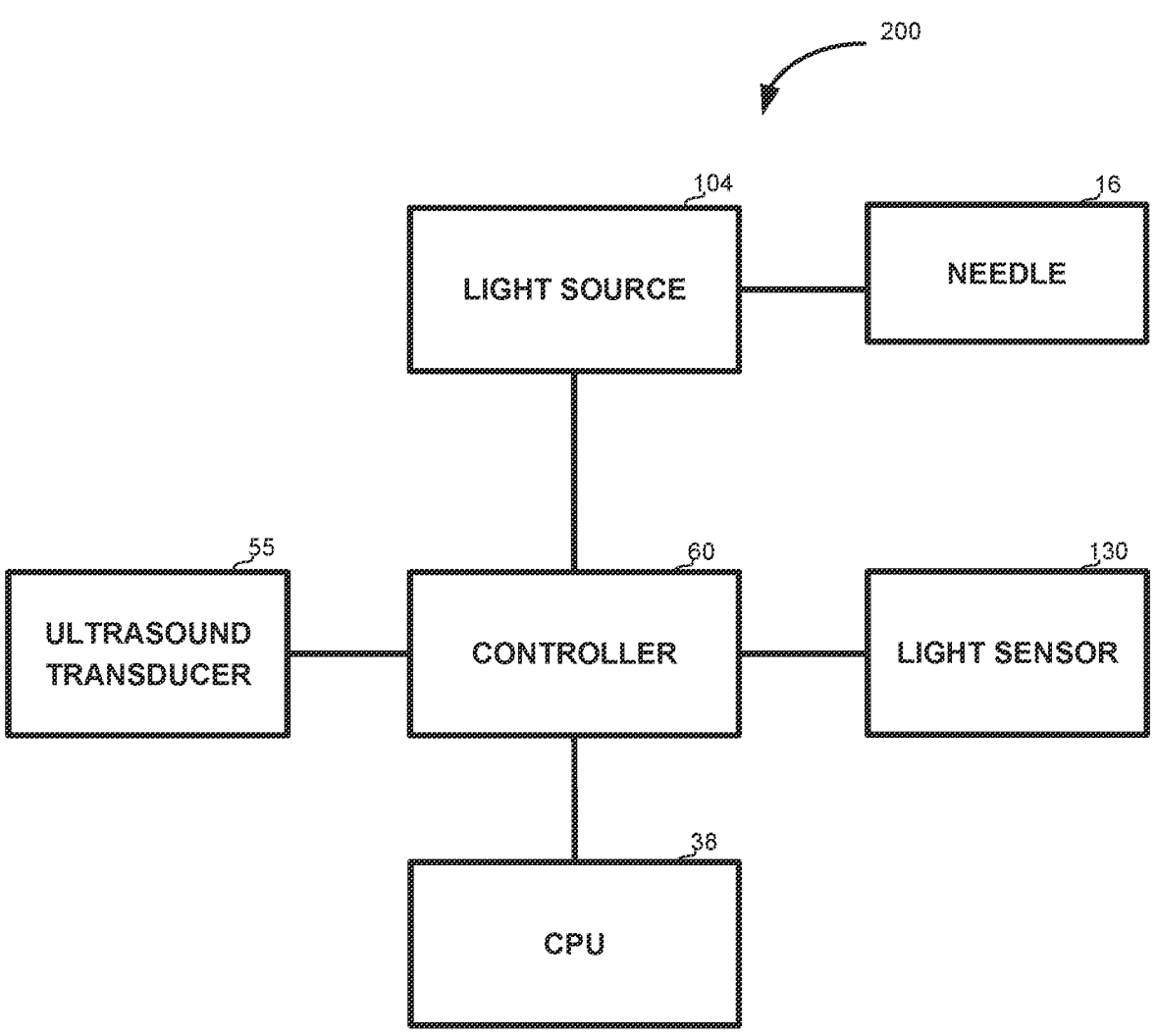
FIG. 2A is a schematic block diagram of a system for activating the ultrasound transducer of a phacoemulsification system, in accordance with light reflection from the eye, in accordance with some exemplary embodiments of the disclosure.

Referring now to FIG. 2A, showing a schematic block diagram of an ultrasound activation system 200 for activating an ultrasound transducer of a phacoemulsification system according to light reflection and detection, in accordance with some exemplary embodiments of the disclosure.

System 200 may comprise light source 104 and light sensor 130 detailed above.

Light source 104 may radiate light in one or more predefined wavelength or wavelength ranges, and in a predefined temporal pattern, such as a square wave having predetermined emittance and non-emittance periods. Light sensor 130 may be sensitive to one or more of the wavelengths emitted by light source 104.

The light measured by light sensor 130 and which correspond in wavelength and pattern to the light emitted by light source 104 may depend on the specific setup, for example on the location of light sensor 130 relative to the user's eye. The measured light may further vary in accordance with whether needle 16 is in contact with the lens or not. Thus, by monitoring the amount of light captured during the emittance periods of light source 104, controller 60 may determine whether needle 16 is in contact with the lens or not, by testing one or more of the conditions described above or in accordance with an output of an AI engine.

Controller 60 may be configured to toggle ultrasound transducer 55 ON/OFF in accordance with whether contact was identified or not.

Controller 60 may be a microcontroller such as a dedicated microcontroller. Controller 60 may thus be a 32-bit microcontroller with fast, e.g., sub-microsecond real-time capabilities, digital signal processing, low-power/low voltage operation, and connectivity, while maintaining a small form factor for example, the STM32 microcontroller, made by STM, which includes a DMA memory and can be used to control powering of the ultrasound transducer. Controller 60 may have processing and memory capabilities and may be configured for toggling ultrasound transducer 55 without the need to engage processor 38 and its associated firmware/software, and thus reduce delays and provide faster response time. However, in some embodiments, controller 60 may also receive commands from processor 38 of console 28.

Controller 60 may be integrated into console 28. In yet further examples, controller 60 may be integrated into phacoemulsification handpiece 25 or into a disposable unit coupled to the handpiece (e.g., an anti-vacuum surge unit). In further examples, controller 60 and drive module 30 may be implemented as a single controller, where the power line for the ultrasound transducer may be connected to one of the outputs of the microcontroller.

The operation parameters and electrical current may be provided to ultrasound transducer 55 by drive module 30, using for example electrical wiring running within cable 33, subject to controller 60 enabling the current provisioning.

Figures 2B, 2C:
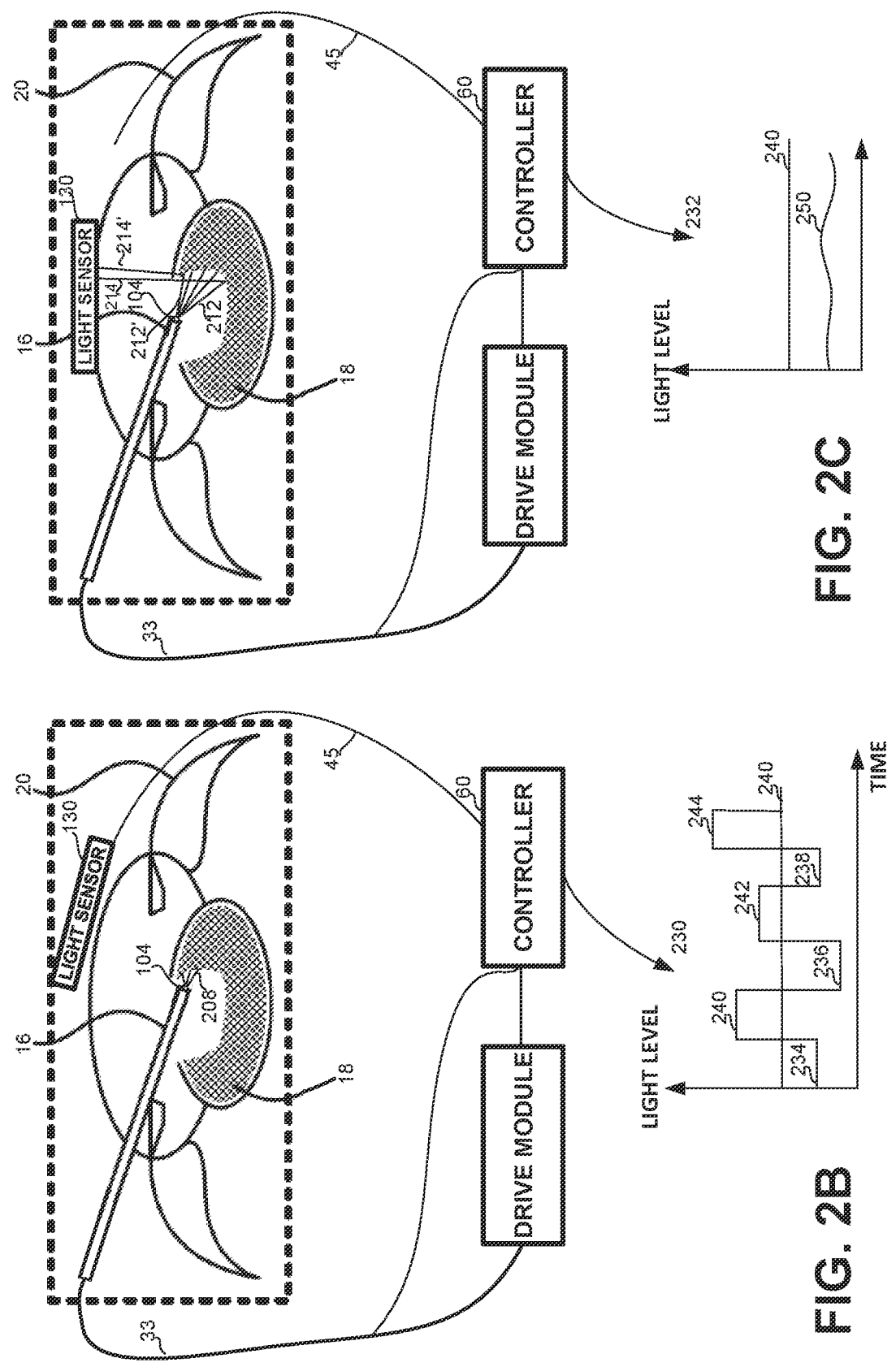
FIG. 2B and FIG. 2C show two exemplary positions of a needle within an eye of a patient and the associated reflected light, in accordance with some exemplary embodiments of the disclosure.

Referring now to FIG. 2B and FIG. 2C, showing schematic illustrations of needle 16 and lens capsule 18 of patient 19, and the activation-related components of the ultrasonic transducer.

In both FIG. 2B and FIG. 2C, needle 16 comprises at its distal tip a light source 104, emitting light in the direction of needle 16 and optionally additional directions. A light sensor 130, sensitive to wavelengths emitted by light source 104 is positioned within the operation room, where it can capture light reflected in response to the light emitted by light source 104. For example, light sensor 130 can be positioned in proximity to eye 20.

Controller 60 may control light source 104 to emit light in a predetermined frequency or temporal pattern by transmitting a signal through cable 33, and receive output from light sensor 130 through cable 45. If, as shown in FIG. 2B, the needle is not in contact with the lens, then emitted light 212 or 212' is reflected from the lens as light 214 or 214'. The amount of reflected light, as output by light sensor 130, may then behave as shown in graph 230, wherein when no light is emitted, the reflected light is as shown in segments 234, 236 and 238, which may be a zero level or another level lower than threshold 240 which may be attributed to the corresponding component of the ambient light. At the periods corresponding to when light source 104 emits light, the reflected light is at a level higher than threshold 240, as shown in segments 240, 242 and 244. It is appreciated that the light level within each segment is not necessarily constant as shown in graph 24 but may vary.

It is appreciated that the light level or distribution thereof may be measured in accordance with other criteria, and is not limited to being above or below threshold 240 as shown. Complying with any other condition as described above. Threshold 240 may be determined in accordance with the specific position of the needle or the sensor, the ambient light, or the like.

If, however, as shown in FIG. 2C needle 16 is in contact with the lens, the no, or very little light is reflected and sensed by light sensor 130, as shown in curve 250 of graph 232.

It is appreciated that it may be first required to receive reflected light above the threshold before needle 16 makes contact with the lens, in order to make sure that when there is no reflected light it is due to the contact and not to a problem in the setup.

Figure 3:
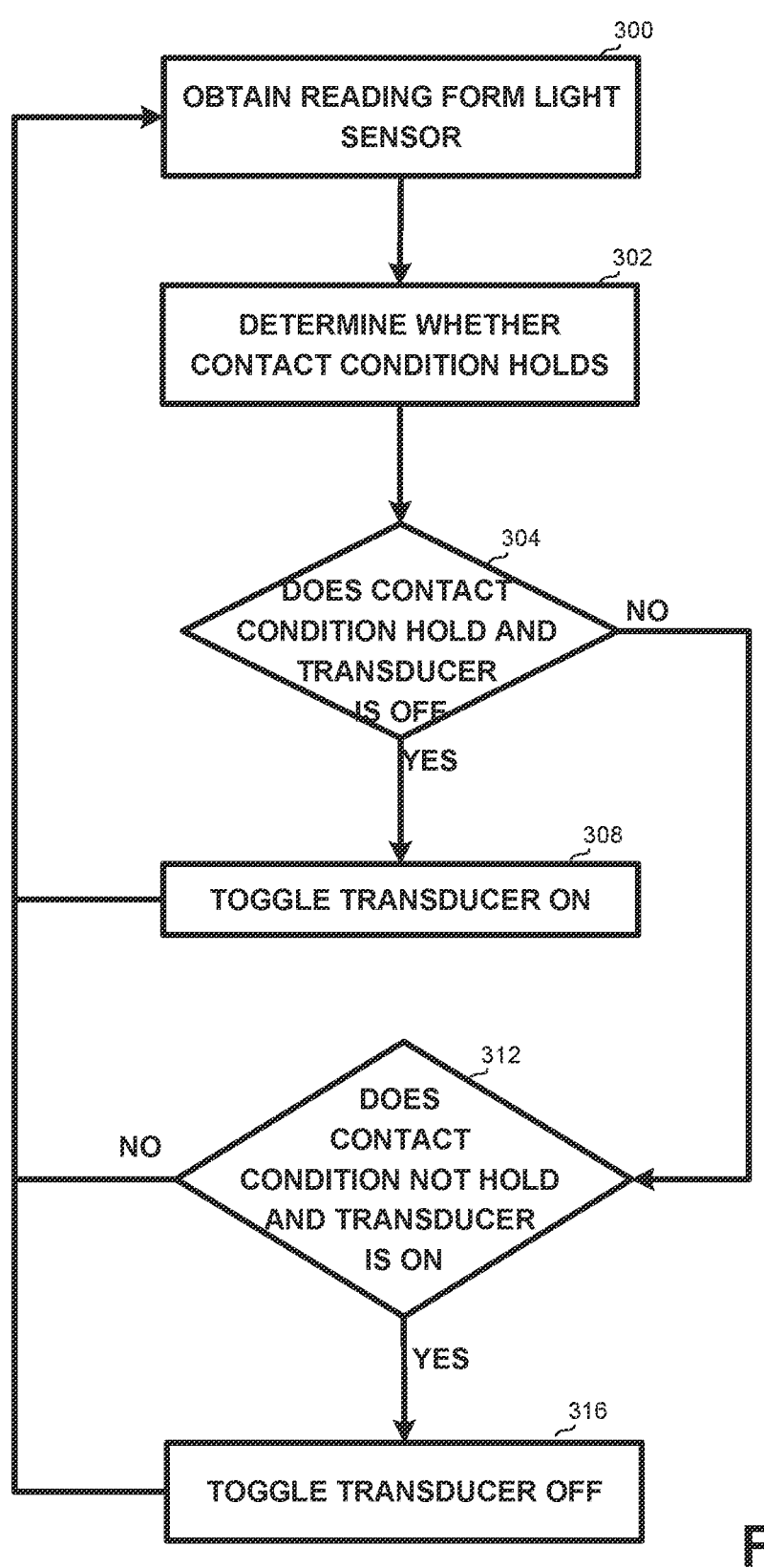
FIG. 3 is a flowchart of steps in a method for operating an ultrasonic transducer during a phacoemulsification operation, in accordance with some exemplary embodiments of the disclosure.

Referring now to FIG. 3, showing a flowchart of a method for operating an ultrasonic transducer, in accordance with some embodiments of the disclosure.

The method of FIG. 3 may be performed by controller 60, processor 38, or any other processor which may be configured to send a toggle signal to ultrasound transducer 55 or affect a power line connected thereto.

On step 300, a reading from light sensor 130 may be obtained. The reading may include a total light level, a light level sensed by one or more pixels, a spatial pattern of the light level, or the like.

On step 302, it may be determined whether the light level received on step 300 complies with a contact condition. For example, the condition may be whether the light level is below a threshold; whether the light level dropped by at least a predetermined quantity or percentage relative to a previous light level, whether the light level derivative is below a threshold; whether the light pattern complies with a predetermined pattern, for example differs in at most a predetermined number of pixels by at most a predetermined value or any other resemblance criteria; or the like, as detailed above. Additionally or alternatively, contact may be determined by a trained AI engine, as detailed above.

On step 304 it may be determined whether the condition holds and the ultrasonic transducer is off (i.e., whether the ultrasonic transducer has not been activated before, or has been stopped), meaning that the needle has just made contact with the lens capsule.

It is appreciated that step 302 may take into account the synchronization between toggling the light source and the light indications received from the light sensor. For example, the received light may be checked only at the time slots when the light source was transmitting light.

If the condition holds ("yes"), i.e., the transducer is off and the output from the light sensor indicates contact, then on step 308, the controller may toggle the transducer ON.

The method may then continue on step 300 with a subsequent output received from the light sensor.

However, if the condition does not hold ("no"), i.e., the transducer is already on, or the light does not comply with the condition, then on step 312 it is determined whether the condition does not hold and the transducer is on, meaning that needle 16 has just lost contact with lens capsule 18.

In this case ("yes"), on step 316 the transducer is toggled OFF.

If not, i.e., the condition holds or the transducer is off, but not both (since this combination has been checked on step

304), then either needle 16 is not in contact with lens capsule 18 and the transducer is OFF, or needle 16 is already in contact with lens capsule 18 and the transducer is ON. In these cases, no change is required in the operation status of the transducer, no toggling is performed, and execution may return to step 300 for obtaining a subsequent reading.

In some embodiments, processor 60 may also receive an indication of the pressure within aspiration channel 46a. If the pressure indicates that the channel is clogged, for example due to a block caused by an aspired piece of cataract, processor 60 may halt all vibrations until the block is released.

It is appreciated that the steps and modules disclosed above are in addition to the software, hardware, firmware or other modules required for operating the probe, displaying the phacoemulsification process, performing other calculations required for example for operating irrigation pump 24 or aspiration pump 26, or the like.

The method of FIG. 3 may be coded as a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembly instructions, instruction-set-architecture instructions, machine instructions, machine dependent instructions, microcode, firmware instructions, state-setting data, or either source code or object code written in any combination of one or more programming languages, programming languages such as Java, C, C++, Python, or others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

Example 1

A phacoemulsification system, comprising: a phacoemulsification probe having a needle at its distal end, the needle configured to be inserted into an eye of a patient, the probe comprising an ultrasonic transducer; an optical fiber transferring light from a light source and having a distal end positioned in proximity to the tip of the needle for emitting light of at least one predetermined frequency or pattern; a light sensor for detecting the light emitted by the optical fiber in the at least one predetermined frequency or pattern; and a processor, configured to repeatedly: receive from the light sensor an indication of the detected light; determine whether the detected light complies with a condition indicating contact between the needle and a lens of the eye, and; subject to determining that the detected light complies with the condition and that the ultrasonic transducer being inactive, toggle the ultrasonic transducer to transmit ultrasonic waves; and subject to determining that the detected light does not comply with the condition and that the ultrasonic transducer being active, toggle the ultrasonic transducer to stop transmitting ultrasonic waves.

Example 2

The phacoemulsification system according to example 1, wherein said determining is based on synchronization between toggling the light source and the indication received from the light sensor.

Example 3

The phacoemulsification system according to example 1, wherein the optical fiber is within an aspiration hollow of the phacoemulsification probe.

Example 4

The phacoemulsification system according to example 1, wherein the light source is positioned within the phacoemulsification probe.

Example 5

The phacoemulsification system of according to example 1, wherein the light sensor comprises one or more photodiodes.

Example 6

The phacoemulsification system of according to example 1, wherein the processor is implemented as a microcontroller.

US 12,697,250 B2

13

Example 7

The phacoemulsification system of according to example 1, wherein the condition is that an amount of the detected light is below a predetermined value.

Example 8

The phacoemulsification system of according to example 1, wherein the condition is that an amount of the light is lower in at least a predetermined quantity or percent than a previous measure.

Example 9

The phacoemulsification system of according to example 1, wherein the condition is that a derivative of the indication of the detected light is below a threshold.

Example 10

The phacoemulsification system of according to example 1, wherein the condition is associated with a spatial distribution or pattern of the detected light over the light sensor.

Example 11

The phacoemulsification system of according to example 1, wherein whether the condition holds is determined by a trained artificial intelligence engine.

Example 12

The phacoemulsification system according to example 11, wherein the condition is that the artificial intelligence engine recognizes whether the reflected light indicates that the probe is in contact with the lens or not.

Example 13

The phacoemulsification system according to example 11 wherein the artificial intelligence engine is trained upon a training set comprising pairs of detected light and a label indicating whether there is contact between the needle and the lens, and wherein the label is obtained in accordance with a physician manually activating the ultrasonic transducer when there is contact.

Example 14

The phacoemulsification system according to example 1, wherein the at least one predetermined frequency is between 50 and 200 Hz.

Example 15

The phacoemulsification system according to example 1, further comprising: an irrigation channel for irrigating the eye with irrigation fluid; an irrigation sensor, which is coupled with the irrigation channel and is configured to measure a parameter indicative of a pressure of the irrigation fluid; and an irrigation pump configured to flow the irrigation fluid to the irrigation channel.

Example 16

The phacoemulsification system according to example 1, further comprising: an aspiration channel for evacuating material from the eye; an aspiration sensor, coupled with the aspiration channel and configured to measure a value indicative of a pressure in the aspiration channel; and an aspiration pump configured to evacuate the material from the aspiration channel.

Example 17

The phacoemulsification system according to example 16, wherein subject to the aspiration sensor indicating a clogging of the aspiration channel, the ultrasonic transducer is toggled OFF.

Example 18

A method for applying phacoemulsification to an eye of a patient, comprising: receiving from a light sensor positioned near an eye of the patient an indication of detected light; determining whether the detected light complies with a condition indicating contact between a needle of a phacoemulsification probe when the needle is inserted into the eye of the patient and a lens of the eye; subject to determining that the detected light complies with the condition and that an ultrasonic transducer comprised in the phacoemulsification probe, toggling the ultrasonic transducer to transmit ultrasonic waves; and subject to determining that the detected light does not comply with the condition and that the ultrasonic transducer being active, toggling the ultrasonic transducer to stop transmitting ultrasonic waves.

Example 19

The method according to example 18, wherein said determining is based on synchronization between toggling the light source and the indication received from the light sensor.

Example 20

A computer program product comprising a non-transitory computer readable medium retaining program instructions, which instructions when read by a processor, cause the processor to perform: receiving from a light sensor positioned near an eye of the patient an indication of detected light; determining whether the detected light complies with a condition indicating contact between a needle of a phacoemulsification probe when the needle is inserted into the eye of the patient and a lens of the eye; subject to determining that the detected light complies with the condition and that an ultrasonic transducer comprised in the phacoemulsification probe, toggling the ultrasonic transducer to transmit ultrasonic waves; and subject to determining that the detected light does not comply with the condition and that the ultrasonic transducer being active, toggling the ultrasonic transducer to stop transmitting Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A phacoemulsification system, comprising:
a phacoemulsification probe having a needle at its distal end, the needle configured to be inserted into an eye of a patient, the probe comprising an ultrasonic transducer;
an optical fiber transferring light from a light source and having a distal end positioned in proximity to a tip of the needle for emitting light of at least one predetermined frequency or pattern;
a light sensor for detecting the light emitted by the optical fiber in the at least one predetermined frequency or pattern; and
a processor, configured to repeatedly:
receive from the light sensor an indication of the detected light;
determine whether the detected light complies with a condition indicating contact between the needle and a lens of the eye;
subject to determining that the detected light complies with the condition and that the ultrasonic transducer is inactive, toggle the ultrasonic transducer to transmit ultrasonic waves; and
subject to determining that the detected light does not comply with the condition and that the ultrasonic transducer is active, toggle the ultrasonic transducer to stop transmitting ultrasonic waves.

2. The phacoemulsification system of claim 1, wherein said determining is based on synchronization between toggling the light source and the indication received from the light sensor.

3. The phacoemulsification system of claim 1, wherein the optical fiber is within an aspiration hollow of the phacoemulsification probe.

4. The phacoemulsification system of claim 1, wherein the light source is positioned within the phacoemulsification probe.

5. The phacoemulsification system of claim 1, wherein the light sensor comprises one or more photodiodes.

6. The phacoemulsification system of claim 1, wherein the processor is implemented as a microcontroller.

7. The phacoemulsification system of claim 1, wherein the condition is that an amount of the detected light is below a predetermined value.

8. The phacoemulsification system of claim 1, wherein the condition is that an amount of the light is lower in at least a predetermined quantity or percent than a previous measure.

9. The phacoemulsification system of claim 1, wherein the condition is that a derivative of the indication of the detected light is below a threshold.

10. The phacoemulsification system of claim 1, wherein the condition is associated with a spatial distribution or pattern of the detected light over the light sensor.

11. The phacoemulsification system of claim 1, wherein whether the condition holds is determined by a trained artificial intelligence engine.

12. The phacoemulsification system of claim 11, wherein the condition is that the artificial intelligence engine recognizes whether the reflected light indicates that the probe is in contact with the lens or not.

13. The phacoemulsification system of claim 11 wherein the artificial intelligence engine is trained upon a training set comprising pairs of detected light and a label indicating whether there is contact between the needle and the lens, and wherein the label is obtained in accordance with a physician manually activating the ultrasonic transducer when there is contact.

14. The phacoemulsification system of claim 1, wherein the at least one predetermined frequency is between 50 and 200 Hz.

15. The phacoemulsification system of claim 1, further comprising:
an irrigation channel for irrigating the eye with irrigation fluid;
an irrigation sensor, which is coupled with the irrigation channel and is configured to measure a parameter indicative of a pressure of the irrigation fluid; and
an irrigation pump configured to flow the irrigation fluid to the irrigation channel.

16. The phacoemulsification system of claim 1, further comprising:
an aspiration channel for evacuating material from the eye;
an aspiration sensor, coupled with the aspiration channel and configured to measure a value indicative of a pressure in the aspiration channel; and
an aspiration pump configured to evacuate the material from the aspiration channel.

17. The phacoemulsification system of claim 16, wherein subject to the aspiration sensor indicating a clogging of the aspiration channel, the ultrasonic transducer is toggled OFF.

* * * * *